(12) United States Patent
Durante et al.

(10) Patent No.: US 12,284,577 B1
(45) Date of Patent: Apr. 22, 2025

(54) SENSOR AND TRANSMITTER COMMUNICATIONS DEVICE AND METHOD OF USE THEREOF

(71) Applicant: Outerlink Corporation, Shreveport, LA (US)

(72) Inventors: Steven J. Durante, Lincoln, MA (US); Thavisouk Nanthavongsa, Leominster, MA (US); Kevin Turner, Concord, MA (US); Rod Danielson, Exeter, NH (US)

(73) Assignee: Outerlink Corporation, Shreveport, LA (US)

( * ) Notice: Subject to any disclaimer, the term of this patent is extended or adjusted under 35 U.S.C. 154(b) by 311 days.

(21) Appl. No.: 17/693,987

(22) Filed: Mar. 14, 2022

Related U.S. Application Data

(60) Provisional application No. 63/160,264, filed on Mar. 12, 2021.

(51) Int. Cl.
*H04W 4/38* (2018.01)
*B64D 1/08* (2006.01)
*G01N 33/00* (2006.01)
*G01W 1/08* (2006.01)
*H04B 7/185* (2006.01)
*H04W 84/12* (2009.01)

(52) U.S. Cl.
CPC ............... *H04W 4/38* (2018.02); *B64D 1/08* (2013.01); *G01N 33/0075* (2013.01); *G01W 1/08* (2013.01); *H04B 7/18513* (2013.01); *H04W 84/12* (2013.01)

(58) Field of Classification Search
CPC .... G01N 33/24; G01N 33/241; G01N 33/246; G01N 2033/243; G01N 2033/248; G01N 2033/245
See application file for complete search history.

(56) References Cited

U.S. PATENT DOCUMENTS

| 2012/0190386 A1* | 7/2012 | Anderson | G01S 19/14 455/456.3 |
|---|---|---|---|
| 2018/0052130 A1 | 2/2018 | Farhart et al. | |
| 2018/0180564 A1 | 6/2018 | Farhart et al. | |
| 2018/0203158 A1* | 7/2018 | Ulmer | G01S 17/86 |

(Continued)

OTHER PUBLICATIONS

Clear Scientific, LLC; A multicomponent indicator ticket for presumptive field identification of hazardous materials; https://www.sbir.gov/sbirsearch/detail/1598689; Small Business Innovation Research (SBIR) and Small Business Technology Transfer (STTR); 2018.

(Continued)

*Primary Examiner* — Herbert K Roberts
(74) *Attorney, Agent, or Firm* — Garvey, Smith & Nehrbass, Patent Attorneys, L.L.C.; Julie Rabalais Chauvin; Fabian M. Nehrbass

(57) ABSTRACT

The present invention relates to a communications device, system, and method of use, having multiple posts or darts that can be dropped (e.g., with a drone) at spaced apart locations to form a communications fence. In one embodiment, the present invention relates to a sensor and transmitter communications device that can create a virtual sensor fence that can include sensor posts or darts and gateway posts or darts.

21 Claims, 12 Drawing Sheets

(56) References Cited

U.S. PATENT DOCUMENTS

2019/0285504 A1* 9/2019 Muralidhar ............. F17D 5/005
2021/0112781 A1* 4/2021 Crouthamel ......... A01K 29/005

OTHER PUBLICATIONS

Clear Scientific, LLC; A multicomponent indicator ticket for presumptive field identification of hazardous materials; https://www.sbir.gov/sbirsearch/detail/1626643; Small Business Innovation Research (SBIR) and Small Business Technology Transfer (STTR); 2019.

* cited by examiner

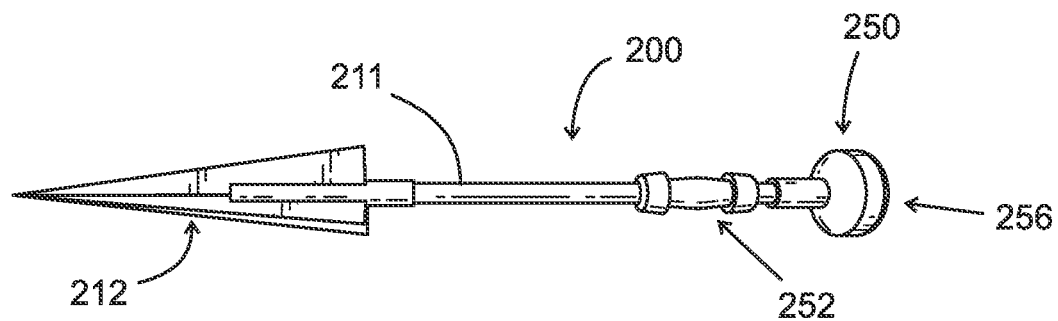
FIG. 15
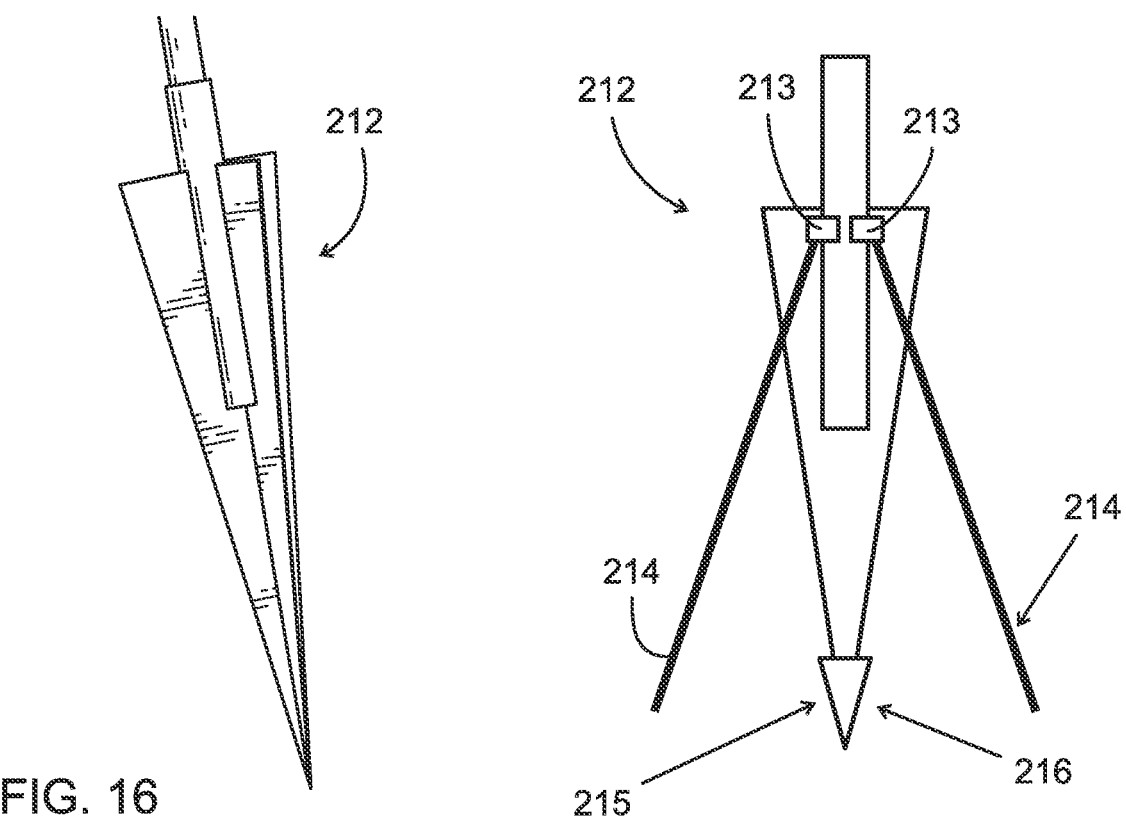
FIG. 16
FIG. 17

SENSOR AND TRANSMITTER COMMUNICATIONS DEVICE AND METHOD OF USE THEREOF

CROSS-REFERENCE TO RELATED APPLICATIONS

Priority is claimed to our U.S. Provisional Patent Application Ser. No. 63/160,264, filed 12 Mar. 2021, which is hereby incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a communications device, system, and method of use. More particularly, the present invention relates to a sensor and transmitter communications device that can create a virtual sensor fence and system, and the method of use thereof.

2. General Background of the Invention

The following possibly relevant U.S. Patent Application Publication Nos. and other references are hereby incorporated herein by reference: US Pat. App. Pub. No. US 2018/0180564; US Pat. App. Pub. No. US 2018/0052130; SBIR Award Contract W911SR-18-C-0017 in 2018 for "A multicomponent indicator ticket for presumptive field identification of hazardous materials"; SBIR Award Contract W911SR-19-C-0016 in 2019 for "A multicomponent indicator ticket for presumptive field identification of hazardous materials."

BRIEF SUMMARY OF THE INVENTION

The present invention relates to a communications device, system, and method of use. More particularly, the present invention relates to a sensor and transmitter communications device that can create a virtual sensor fence and system, and the method of use thereof.

The apparatus of the present invention relates to a rapidly deployable multi-modal communications device that can serve as a virtual sensor fence for interrogating or detecting environmental conditions such as humidity, temperature, wind, and/or particulants in the air that may be hazardous or deadly. The system of the present invention includes multiple sensor posts or darts that can be launched, dropped (e.g., using drone(s)), or deployed by hand within a selected distance or spacing, for example, a spacing of 500 meters between each other).

Once deployed, each sensor post or dart can preferably communicate with one or more of the other sensor posts or darts in a chain to create a system including multiple redundant communications hubs that are connected to, for example an LTE network, or a satellite transceiver.

The sensor posts or darts preferably include sensor arrays, processors, batteries and associated circuitry in a disposable housing/package/shell/tube/container (such as cardboard) designed to pierce the ground/lawn/earth's surface if dropped. Alternatively, each post can have a weighted circular tip (e.g., rubber, polymer, plastic) to stand upright.

Each sensor post or dart can be preferably equipped with mesh network and Wifi capabilities that receive environmental data and transmit to multiple sensor post hubs that can transmit the acquired data over LTE or satellite communications, for example. The sensor post fence apparatus of the present invention is designed to be a leave behind communications module with multiple modes of communications. Attached to these communications devices can be one or more environmental sensors that can sense humidity, temperature, wind, direction, GPS, orientation, and/or particulants in the air that may be hazardous or deadly. The mesh network is for each virtual "fence post" or "sensor post" to communicate with each other in a daisy chain manner. This allows data to be bounced from post to post until the data reaches a wide area communications upload point (e.g., LTE or SatCom). Wifi capabilities allow a single "fence post" to be communicated with directly from a tablet or a smartphone for data interrogation to connect to a wider area network, such as LTE or SatCom (satellite communications), to do updates or to use a short range single node to operate independently.

In a preferred embodiment of the present invention, each sensor post, dart, or device can communicate with another sensor post or dart as follows: a post or dart can communicate using its Mesh network (LoRa) as a wide area private network. LoRa is a low power wide area network modulation technique. It is based on spread spectrum modulation techniques derived from chirp spread spectrum technology. LoRa is known in the art. In one embodiment, these communications can only send and receive to each other. Certain variants or alternative embodiments of the apparatus and system of the present invention can include a LoRa gateway that can send/receive messages from outside of the private wide area network (for example, if the posts or darts are positioned in a line over the course of a longer distance (e.g., 5 miles)). If the first post or dart tips over, its gyroscope can trigger a message that can be sent to the next closest group of sensors on the mesh network with its ID, global positioning system (GPS), and notification. The messages can be relayed until they reach a post or dart with a gateway component that transports the ID, GPS and notification/messages over satellite or LTE to a remote communications facility anywhere outside of the wide area for rapid decision making response. In a similar fashion, the remote communications facility can send a message back to the fallen device/post by reversing the communications path for further instructions (which could be, for example, "blow in place" (BIP) and destroy).

The apparatus of the present invention is preferably also part of a larger IoT sensor platform that includes connectivity to a communications system. The present invention can advantageously be used with sensor elements having the following capabilities: the system is comprised of a series of mesh networked nodes that communicate with each other creating a virtual sensor fence. The virtual sensor fence can be deployed without wires to interrogate or probe for certain details about the atmosphere. Certain nodes can have additional communications capabilities to transmit or interrogate data from the sensor/post up or down from LTE, Satellite or RFID, Infrared connections. This allows virtual fence nodes to report unique ID, location, weather, wind, time, sensor connection, battery, orientation or penetration as well as being capable of sending messages to disengage, illuminate, excite, or self-destruct specific nodes or darts, for example. The system of the present invention can include nodes which can act as virtual markers or points of interest to create a digital path. This can include modifications imagery or motion sensing.

The apparatus of the present invention provides multiple posts or darts. Each post or dart preferably has a dart or rocket-like general shape, but can be shapes other than like a dart or rocket. Each post or pillar can include an antenna, Comms 2, Comms 1, a processor, batteries, a weight, and optionally, a sensor trigger, such as the "Dominator" or Clear Scientific sensor trigger (that can function using a Clear Sci sensor element). Alternative sensors can be used in place of the "Dominator" to trigger other environmental sensors, as this device can be adapted for other uses requiring mesh communications tethered to a wide area gateway operating over the network (e.g., Outerlink network). The "Dominator" is made by Clear Scientific.

An alternative embodiment of the apparatus of the present invention can include a base (e.g., rubber, polymeric, plastic) that provides a selected weight or has a weight in it.

The apparatus of the present invention can be rapidly deployable (e.g., air dropped) from a drone or rotorcraft, or similar device, for example. Once dropped, each post or device can fall to the earth and become at least partially submerged within the earth's surface or underlying terrain, preferably with the weighted end of the post embedded in the earth. Alternatively, the apparatus of the present invention can be deployed from a drone or rotorcraft or similar device and land on or on top of the earth's surface, but not be at least partially submerged within the earth's surface, such as on a rocky surface.

The apparatus of the present invention can provide multiple posts or darts, wherein each post or dart can be disposable and can be battery powered.

The present invention preferably includes a mesh networked communications to a satellite backhaul, which can include a Comms 1 Mesh to connect each device and a Comms 2 Satellite event uplink. The satellite uplink can be delivered by an Iridium satellite modem connected to the Outerlink satellite communications system. A mesh communications can exist between each post. When an "event" occurs, that data gets uplinked to a satellite. Examples of "events" include, but are not limited to, verification of wind direction or identification of certain chemical elements in the air. Each post of the present invention can also include chemical sensors and/or bio-sensors.

A preferable method of use of the present invention includes using multiple posts or darts to create or comprise a virtual sensor fence. Preferably, each post or dart is spaced a selected distance from another post or dart (e.g., maximum of about 1640 feet apart (for example, 1000 feet apart)) with a redundant wide area communications channel (LTE, Sat) approximately at about 5000 feet.

The apparatus of the present invention can also include a portable or wearable handheld communications device. In a preferred embodiment, the portable or wearable handheld communications device can communicate a GPS location (e.g., of a person carrying or holding the device) to a satellite or LTE network. In a preferred embodiment, the portable or wearable handheld communications device can transmit information over a satellite or LTE network, wherein said information is preferably gathered from a sensor.

In one embodiment, the portable or wearable handheld device can be called a Standard G4 and can be a tracking device that operates over LTE and satellite. In a preferred embodiment, the Standard G4 is operated by plugging it into a cigarette lighter, and its GPS position can be sent over LTE or satellite.

In an alternative embodiment, the portable or wearable handheld device is a variant of the Standard G4 and uses the capabilities of the G4 instead of simple GPS positional information. In a preferred embodiment, the variant of the portable or wearable handheld communications device can include a microprocessor that can process other environmental data from other sensors that it is connected to. In a preferred embodiment, the microprocessor can serve as a computer that can store, process, transmit, and receive data from other environmental sensors that it is connected to either with a wire connection or a wireless connection. In a preferred embodiment, the variant of the portable or wearable handheld communications device can include batteries in addition to the microprocessor and can include other components (e.g., temperature, acceleration, impact, orientation, humidity, wind).

In an alternative embodiment, the portable or wearable handheld communications device can also include a Clear Scientific ("Clear Sci") Dominator trigger and trigger software. This device can be called CARDS (Clear Alert Rapid Detection System). In a preferred embodiment, the CARDS device can include an LED light (e.g., a red LED light) that flashes on the device indicating that the sensor has been triggered. In a preferred embodiment, an alert can be defined by an end user in a configuration set up, but generally, an alert can be defined by sending a message over satellite, LTE, WiFi or Long Range WiFi known as Mesh networking. In a preferred embodiment, the CARDS device can also include a USB port to install and run software updates. In a preferred embodiment, the CARDS device can also include an LTE Whip antenna that can be used to transmit data to the Outerlink network. In a preferred embodiment, the CARDS device can also include a GPS antenna so that the device can acquire a GPS signal for the purpose of sending and receiving time and position of the device. In a preferred embodiment, the CARDS device can also include a sensor shield that protects the sensor. An example of using the CARDS device can include an end user placing a CARDS device in an area where he/she believes that the area has been contaminated with a chemical substance. The CARDS device includes an installed Clear Alert Sensor element that can detect the presence of the chemical and transmit an alert consisting of a flashing light or message sent via LTE, Satellite, WIFI or Long Range Wifi (mesh network).

In an alternative embodiment, the portable or wearable handheld communications device does not include a Clear Scientific ("Clear Sci") Dominator trigger, and said device can be called CQ5. In a preferred embodiment, the CQ5 device can include an SD card reader that can be used for installing and running new or updated software to the microprocessor. In a preferred embodiment, the CQ5 device can include a temperature sensor that helps the software compensate for external changes in temperature. In a preferred embodiment, the CQ5 is a battery operated IoT sensor platform. An example of using a CQ5 device can include sending GPS position reports from a vehicle, transmitting the heart rate of the driver, and sending an alert when the driver's heart rate exceeds thresholds (high or low) while the vehicle is moving. Therefore, the CQ5 can ingest and send data from a body worn device in addition to sending GPS position data. The CQ5 device can include a communications layer to the Outerlink gateway and common operating system.

The present invention includes a sensor fence apparatus, comprising a plurality of dart or rocket shaped posts or darts; each dart or post having a housing, shell, or fuselage with an interior; at least one sensor located on the exterior of the fuselage; at least one processor located within the interior of the fuselage; each post or dart having a power source; each post having an output device, wherein in use each said post or dart is in contact with the earth's surface or an underlying terrain; wherein said at least one sensor senses one or more of the following environmental parameters: humidity, temperature, wind, and particulants in the air that may be hazardous or deadly; and wherein said output device transmits said one or more environmental parameters to one or more others of said posts or darts. The present invention includes a sensor fence apparatus having an output device, wherein the output device transmits one or more environmental parameters over an LTE network and/or via satellite communications. The present invention includes a sensor fence apparatus having an output device, wherein the output device transmits one or more environmental parameters to one or more others of said posts or darts via a mesh network. The present invention includes a sensor fence apparatus further comprising WiFi capabilities that allow for each post or dart to communicate with a tablet or smartphone or to connect to a wider area network, such as an LTE or satellite network. The present invention includes a sensor fence apparatus further comprising WiFi capabilities that allow for each post or dart to communicate with a tablet or smartphone or to connect to a wider area network, such as an LTE or satellite network.

The present invention includes a sensor fence apparatus further comprising an antenna on one or more of said posts or darts. The present invention includes a sensor fence apparatus having an output device, wherein the output device transmits one or more environmental parameters over an LTE network and/or via satellite communications. The present invention includes a sensor fence device, further comprising a weighted tip at one end of each housing, shell, or fuselage, wherein the weighted tip includes a rubber, plastic, or polymeric material. The present invention includes a sensor fence apparatus, comprising at least one sensor wherein the at least one sensor is a CBRN sensor. The present invention includes a sensor fence apparatus, comprising a housing or fuselage that includes a plurality of fins attached to the exterior of one end of the housing or fuselage, and further comprising at least one sensor, wherein the at least one sensor is attached to a fin. The present invention includes a sensor fence apparatus, further comprising a chemical sensor and/or a bio-sensor.

The present invention includes a sensor fence system, comprising a plurality of spaced apart communications devices including sensor posts or darts; each said dart or post having the ability to communicate with one or more other of said posts or darts; wherein said communications devices each collect and transmit environmental data that includes or more of the following parameters: humidity, temperature, wind, and particulants in the air that may be hazardous or deadly; and wherein said communications devices are connected to an LTE network.

The present invention includes a sensor fence system, comprising a plurality of spaced apart communications devices including sensor posts or darts, and gateway posts or darts; wherein said communications devices communicate with each other to collect and transmit selected environmental data; and wherein said communications devices are each connected to a satellite transceiver. The present invention includes a method of collecting and monitoring environmental data of claim using the aforesaid sensor fence system.

The present invention includes a sensor and transmitter communications device comprising a shell or container, at least one sensor located on the exterior of the shell, at least one processor located within the interior of the shell, a power source, and an output device, wherein in use said communications device is in contact with ground or soil, wherein said at least one sensor senses environmental data, and said output device transmits said environmental data. The present invention includes a sensor and transmitter communications device comprising an output device, wherein the output device transmits environmental data over an LTE network. The present invention includes a sensor and transmitter communications device comprising an output device, wherein the output device transmits environmental data via satellite communications. The present invention includes a sensor and transmitter communications device further comprising a mesh network. The present invention includes a sensor and transmitter communications device further comprising WiFi capabilities. The present invention includes a sensor and transmitter communications device further comprising WiFi capabilities. The present invention includes a sensor and transmitter communications device further comprising an antenna. The present invention includes a sensor and transmitter communications device comprising an output device, wherein the output device transmits environmental data over an LTE network. The present invention includes a sensor and transmitter communications device comprising an output device wherein the output device transmits environmental data via satellite communications. The present invention includes a sensor and transmitter communications device further comprising a weighted tip at one end of the container. The present invention includes a sensor and transmitter communications device further comprising a rubber piece or end connected to the weighted tip. The present invention includes a sensor and transmitter communications device comprising at least one sensor, wherein the at least one sensor is a CBRN sensor. The present invention includes a sensor and transmitter communications device comprising a container and at least one sensor, wherein the container includes a plurality of fins attached to the exterior of one end of the container and, wherein the at least one sensor is attached to a fin. The present invention includes a sensor and transmitter communications device further comprising a chemical sensor and/or a bio-sensor.

The present invention includes a method of collecting and monitoring environmental data using a sensor fence apparatus. The present invention includes a method of collecting and monitoring environmental data using a sensor fence system, comprising: a plurality of spaced apart communications devices including sensor posts or darts; each said dart or post having the ability to communicate with one or more other of said posts or darts; wherein said communications devices each collect and transmit environmental data that includes or more of the following parameters: humidity, temperature, wind, and particulants in the air that may be hazardous or deadly; and wherein said communications devices are connected to an LTE network.

The present invention includes a method of collecting and monitoring environmental data using the aforesaid sensor and transmitter communications devices.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIGS. 15-17 show an alternative embodiment of the apparatus of the present invention and its components.

DETAILED DESCRIPTION OF THE INVENTION

Figure 3:
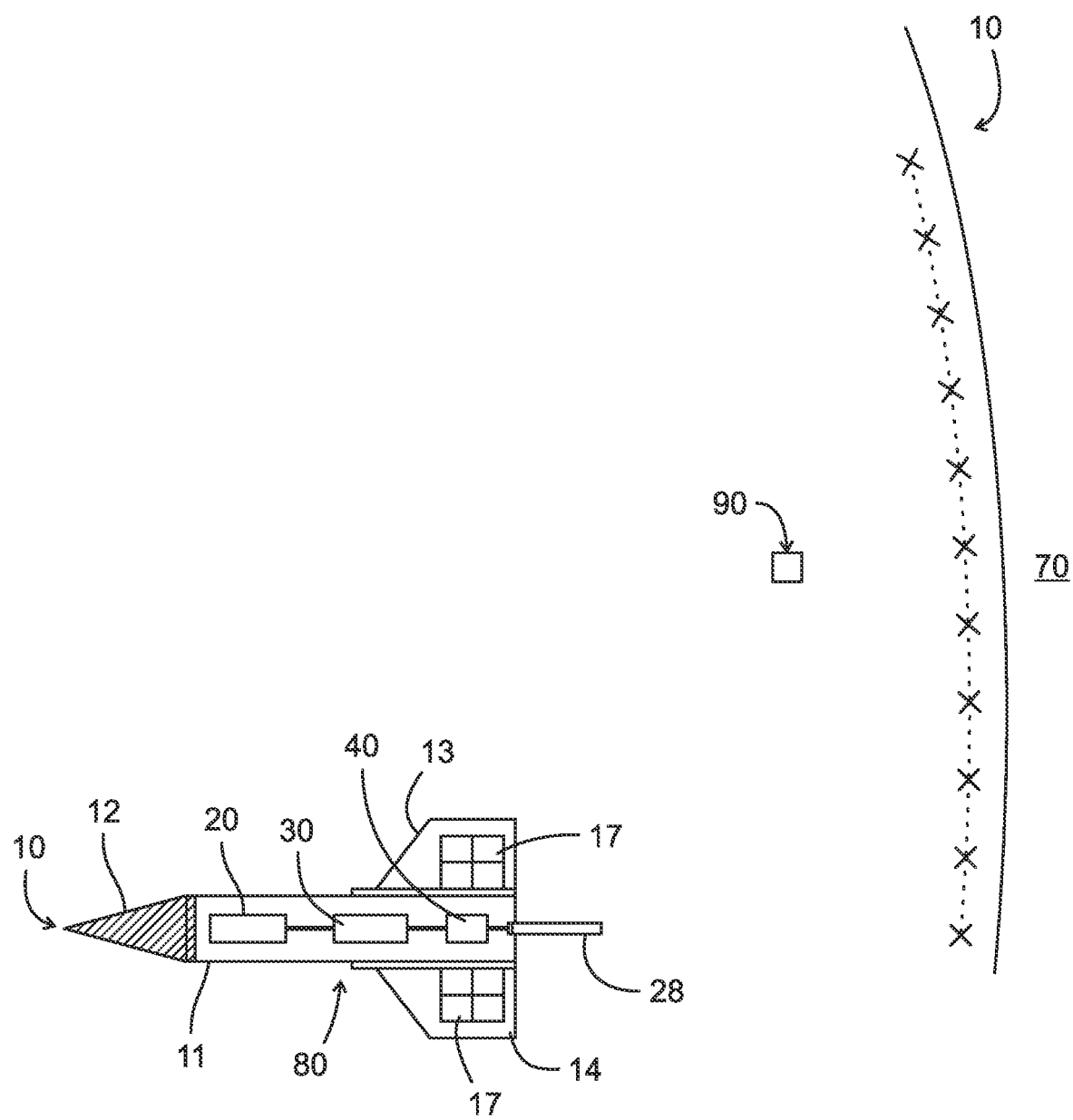
FIG. 3 is a schematic diagram of a preferred embodiment of the apparatus and the system of the present invention.

FIG. 3 shows a preferred embodiment of the apparatus of the present invention, designated generally by the numeral 10. The present invention provides a sensor fence 16, 23 (shown in FIGS. 5 and 14, for example) that includes multiple communication devices in the form of posts or darts 10, 15, 100, 200 as described more fully herein. Each communication device/sensor post or dart 10 can be generally rocket-shaped or dart-shaped having a forward cone shaped nose 12, tubular body or tube 11 and multiple aft fins 13, 14. In a preferred embodiment (as seen in the figures, for example), sensor post or dart 10 can include housing, fuselage, or tube 11, with nose or cone 12 at a forward end of tube 11 and fins 13, 14 preferably located at the rear end of body 11, i.e., at the opposite or distal end of tube 11 from nose or head 12. In a preferred embodiment of the apparatus of the present invention, each fin 13, 14 can have a sensor 17 on it. Sensor 17 can be a CBRN/CSI sensor, for example. As seen in FIG. 3, antenna 28 can be located between fins 13, 14. Battery 20 can be located within fuselage 11. Battery 20 powers device 10. Battery 20 can be multiple batteries in a single package, grouped together in a bundle or in a line. There can be, for example, up to three 3.7 volt batteries.

The embodiment of apparatus 10 shown in FIG. 3 can include a central gateway 90 (which can be called a Central Node), which is preferably part of a mesh communication network. The mesh network allows one post or dart 10 to communicate with one or more other posts or darts 10. Multiple posts or darts 10 can communicate with other posts or darts 10 and additionally communicate with a secondary network if an additional central gateway or central node is added. This additional central gateway or central node 90 aggregates and disburses the data received from all of the posts or darts that are part of the network.

Figure 1:
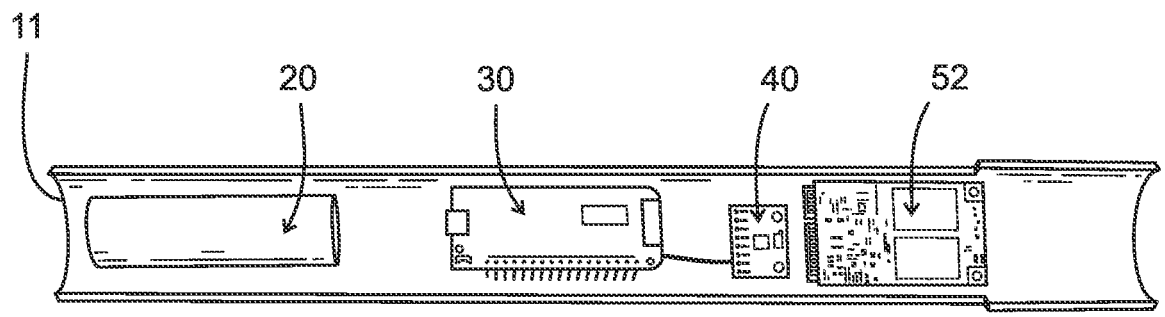
FIGS. 1 and 2 are schematic diagrams of a preferred embodiment of the apparatus of the present invention, including, two cut away views of the housing or tube and components therein.
Figure 2:
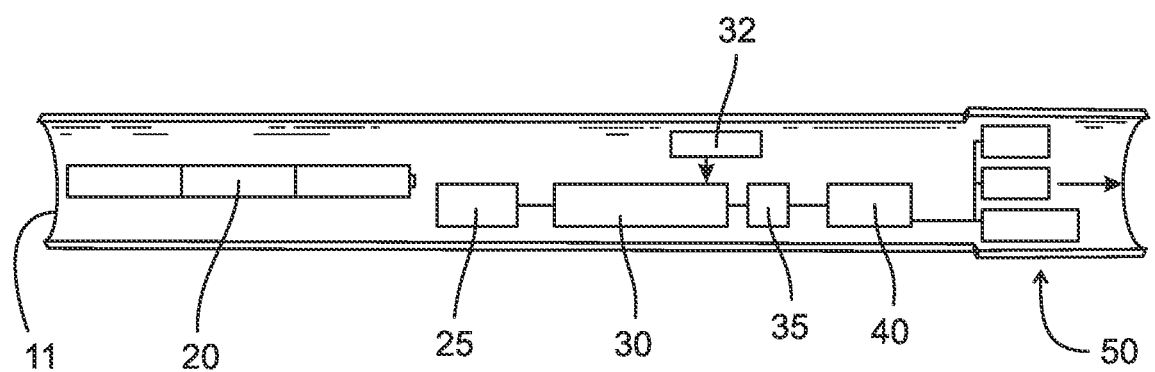

Also preferably located within housing or fuselage 11 is processor 30, which is operatively connected to battery 20, as shown in FIGS. 1-3, for example. Processor 30 can be commercially available such as an RF microcontoller based processor. Processor 30 is preferably the primary processor that is used to process, store, send, and receive data. Apparatus 10 can also include embedded environmental sensors 80, such as a wind long range sensor (also known as a Wind Lora). Also located within fuselage 11, and preferably operatively connected to processor 30, is analog to digital converter 40, as shown in FIGS. 1-3, for example. Analog sensor component of converter 40 receives signals that are read by a current of electricity. These signals are converted by converter 40 into a digital signal that can be passed to processor 30 that, in turn, can trigger a message to be sent over one of the communication links (Wifi, Long Range (LoRa), LTE, Bluetooth, or satellite).

FIGS. 1 and 2 show cutaway views of preferred embodiments of the apparatus 10 of the present invention, showing the housing, fuselage, or tube 11 and components therein, which can include a plurality of batteries 20, battery charging circuit 25, processor 30 (which preferably includes associated Mesh/LTE/Bluetooth/WIFI communications; processor 30 also preferably includes internal memory and software required to send and receive messages to and from a network such as the Outerlink network), accelerometer 35, analog/digital converter 40, and an area 50, preferably located distally from the location of batteries 20, for external outputs for antennae, solar and sensor trigger(s) 52.

Batteries 20 are preferably operatively connected to battery charging circuit 25. Batteries 20 can be multiple batteries in a single package, grouped together in a bundle or in a line, and there can be for example up to three 3.7 volt batteries. Processor 30 can be a commercially available RF microprocessor such as Model No. ESP32. Part of processing unit/processor 30 is mesh network communication protocol/long range (LoRa) 32. Protocol 32 is similar to WiFi. Analog/digital converter 40 converts current into a digital signal. Converter 40 can be a satellite communications modem, preferably a short burst satellite data modem, commercially available from IRIDIUM Communications. Trigger 52 can be a Clear Scientific Dominator trigger that is used for sensing chemicals in the atmosphere. Accelerometer 35 is preferably operatively connected to processor 30 and analog to digital converter 40.

Figure 4:
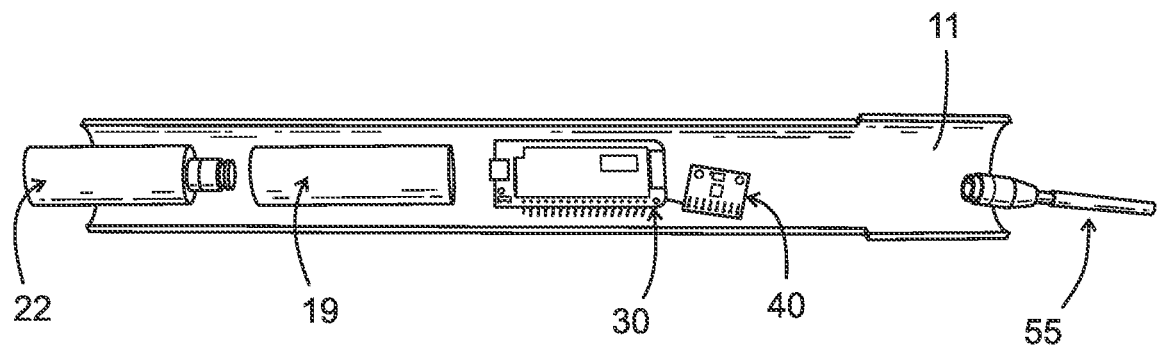
FIG. 4 is an alternative schematic diagram of a preferred embodiment of the apparatus of the present invention, including a cut away view of the housing or tube and components therein.

FIG. 4 is an alternative embodiment of the apparatus of the present invention. In FIG. 4, there is a cut away view of fuselage 11 and components therein: antenna 22, batteries 19, processor 30, and analog/digital converter 40. The alternative embodiment of the present invention shown in FIG. 4 also can include a chemical/bio sensor 55.

Figure 5:
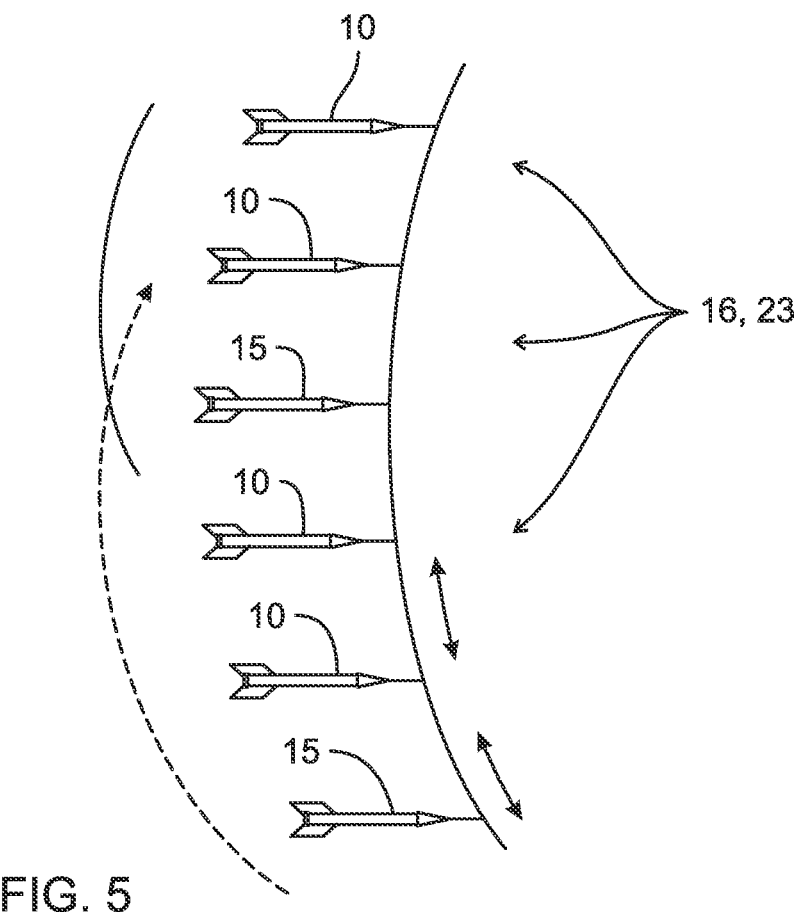
FIG. 5 shows a diagram of a preferred embodiment of the system of the present invention showing placement of gateway posts or darts embedded in the ground/lawn in relation to sensor posts or darts that are also embedded in the ground.
Figure 6:
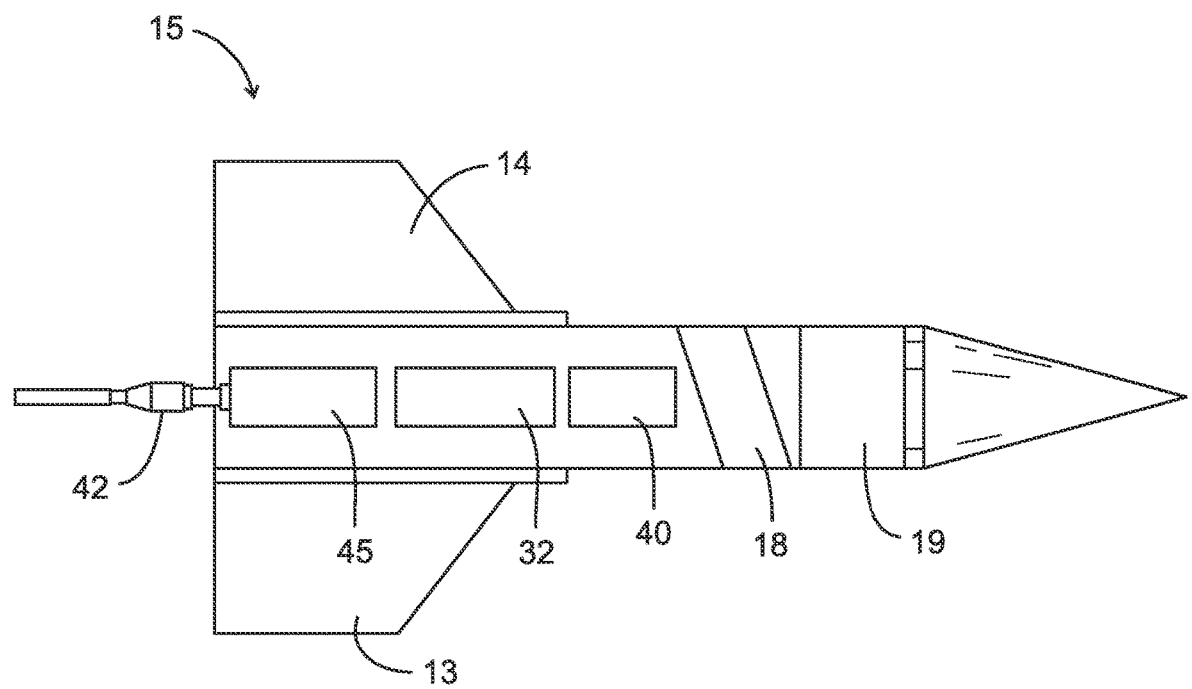
FIG. 6 shows a preferred embodiment of the gateway dart or post apparatus of the present invention.
Figure 7:
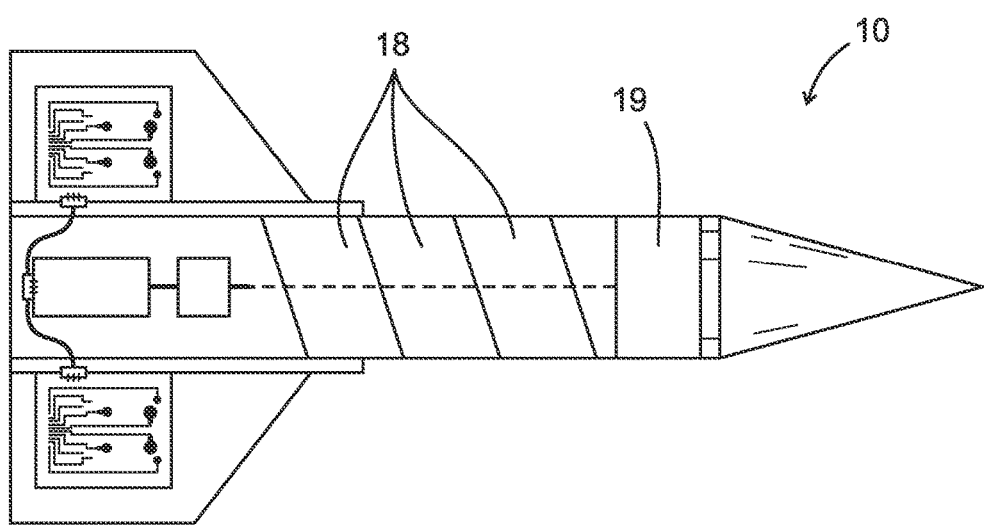
FIG. 7 shows an alternative embodiment of the apparatus of the present invention.

FIG. 5 shows an alternative embodiment of sensor fence 16, 23 of the present invention. FIG. 6 shows a gateway variant of the present invention. This gateway variant 15 is preferred for use for the virtual sensor fence apparatus or system 23 that is comprised of both multiple sensor posts or darts 10 (and/or 100 and/or 200) and multiple gateway darts or devices 15. FIGS. 6 and 7 show preferred embodiments of a gateway post or dart 15 and a sensor post or dart 10. In FIG. 5, one or more sensor posts or darts 10 and one or more gateway posts or darts 15 communicate and function as a single system 23. The gateway variant 15 can include a satellite modem, antenna 42, and mesh gateway. Antenna 42 is preferably a GPS antenna. Alongside the antenna can be a solar panel or solar tape 18 that resides on top of the gateway variant device, dart or post 15. The solar panel or solar tape 18 is used to trickle charge the batteries 19 for extended battery 19 life. Solar tape 18 can also be included in post 10, as seen in FIG. 7, for example. The gateway variant of FIG. 6 can include a printed circuit board (PCB) 45 that can include a trigger, digital to analog converter, and processor. The gateway variant 15 can also include a converter 40, which is preferably a satellite communications modem. The gateway variant post or dart 15 can also include a "Blow in Place" (BIP), which is part of a method of sending a message to the gateway variant that directs the batteries to heat up and destroy the gateway variant 15 where it stands. In a preferred embodiment, the BIP is a software command sent to the unit or post 15 from a remote location or a command center. Gateway device 15 can have fins 13, 14.

Figure 8:
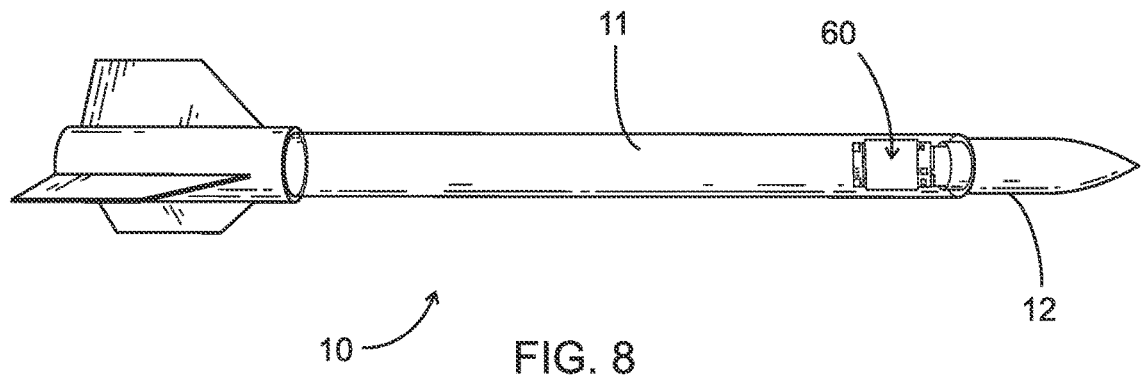
FIG. 8 is a side view of a preferred embodiment of the apparatus of the present invention showing one post or dart.

FIG. 8 is a preferred embodiment of the apparatus of the present invention and shows an option for the fitting of the modem 60, which can be a satellite communications modem. The placement of modem 60 within body 11 can change based on proximity to other components. As shown in FIG. 8, device or pillar 10 can have more than two fins.

Figure 9:
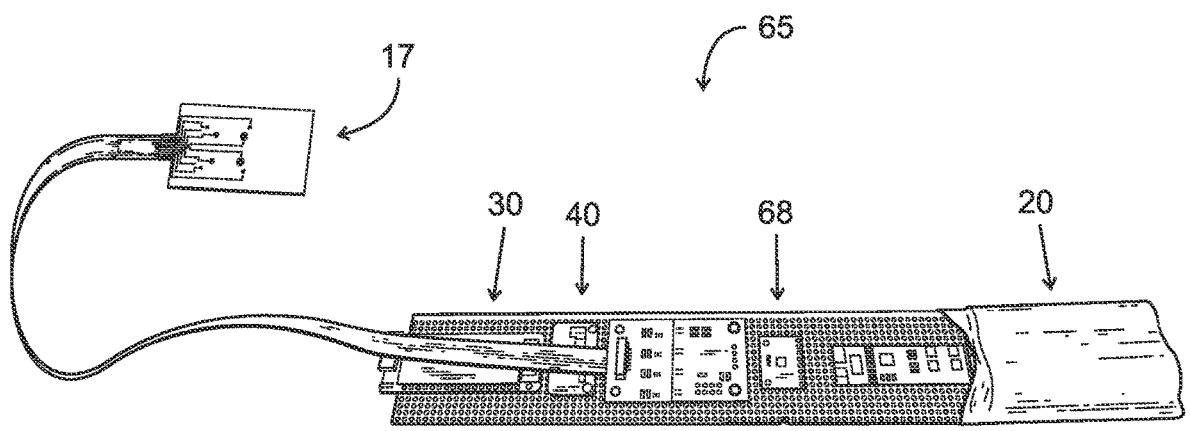
FIG. 9 shows a fragmentary view of a preferred embodiment of the apparatus of the present invention, specifically the leave behind device/circuitry and more specifically, an unpackaged layout of each of the components.
Figure 10:
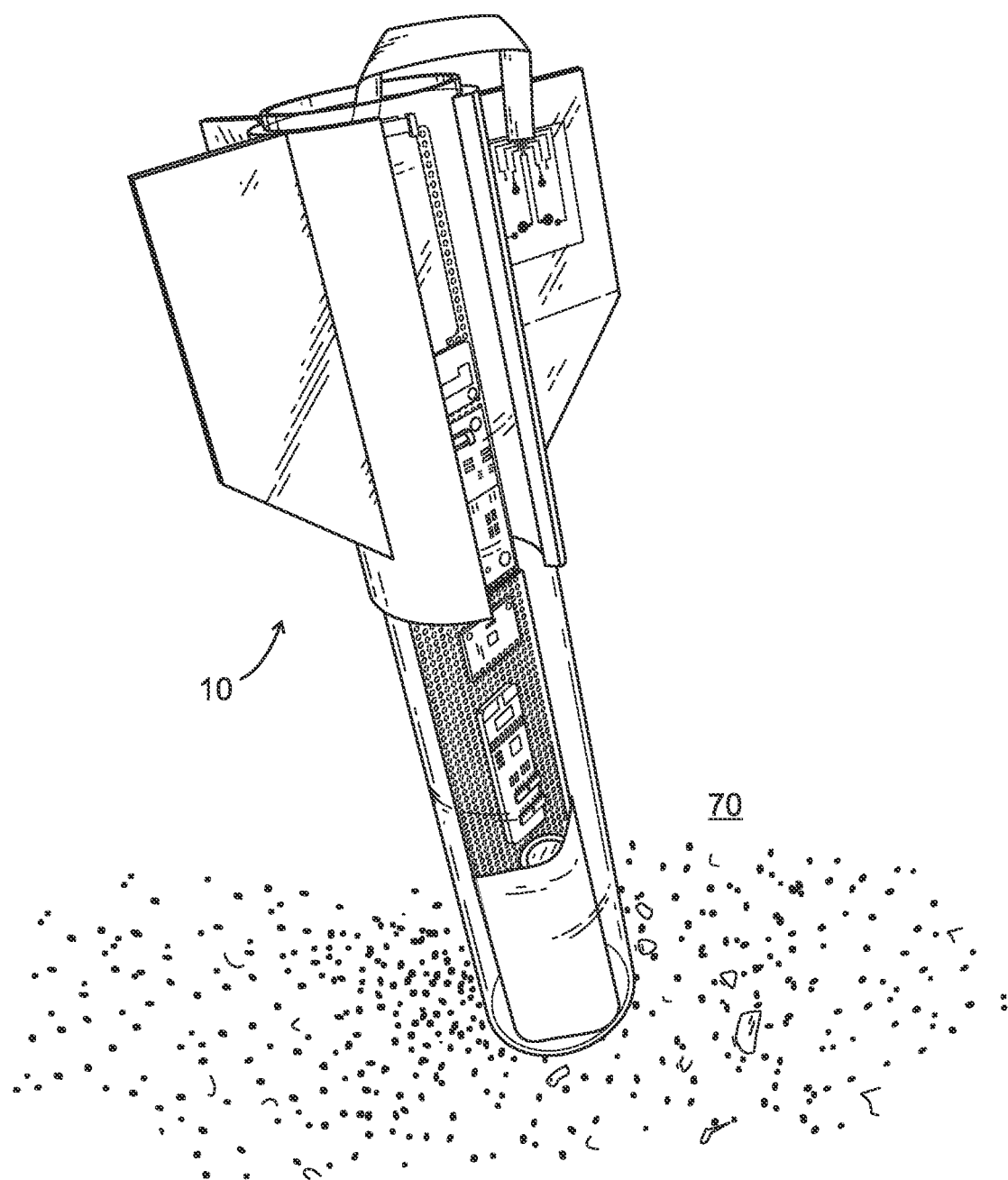
FIG. 10 is a view of a preferred embodiment of the apparatus of the present invention showing a post or dart partially embedded in the ground or earth's surface.
Figure 11:
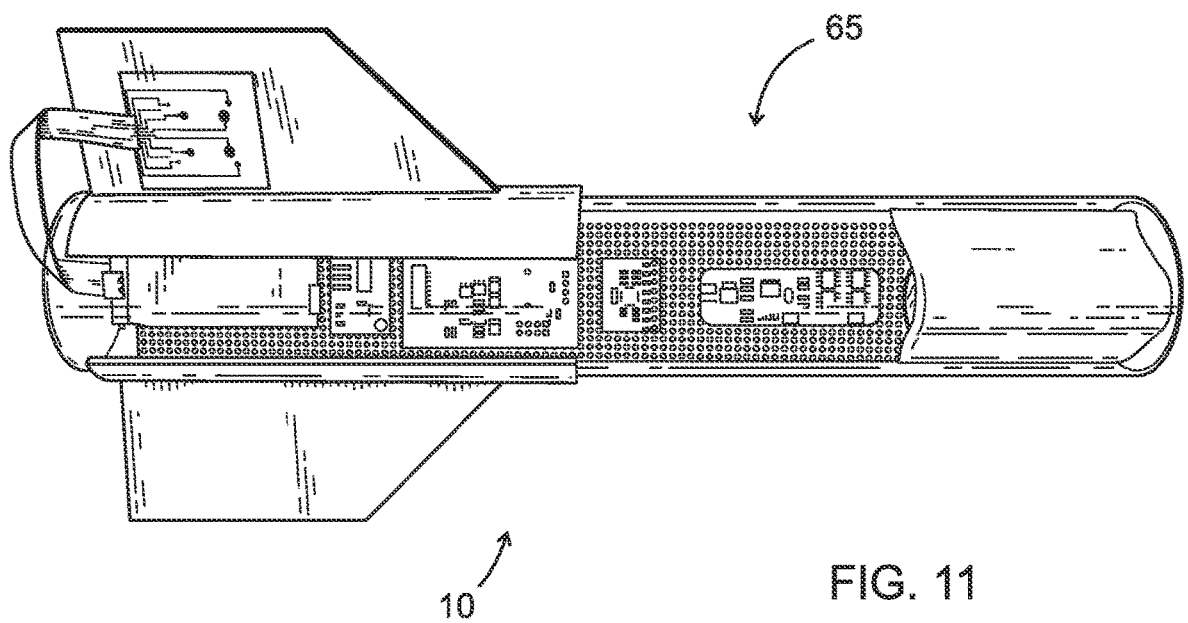
FIG. 11 is a side view of a preferred embodiment of the apparatus of the present invention, including the leave behind device/circuitry inserted within the sensor post or dart.

FIG. 9 shows a fragmentary view of a preferred embodiment of the apparatus of the present invention, specifically the leave behind device/circuitry 65 and more specifically, an unpackaged layout of each of the components. As shown in FIG. 9, leave behind device 65 preferably includes processor 30, converter 40, gyroscope 68, battery 20, sensor 17, and sensor trigger 52 all operably connected to each other. Leave behind device/circuitry 65 can be seen within housing 11 of communication device 10 in FIGS. 10 and 11, with FIG. 10 also showing device 10 as partially embedded in the ground or earth's surface 70. Placement of a single or more than one device 10 allows it to function as a single tethered fence 23 and allows for communication between devices 10.

Figure 12:
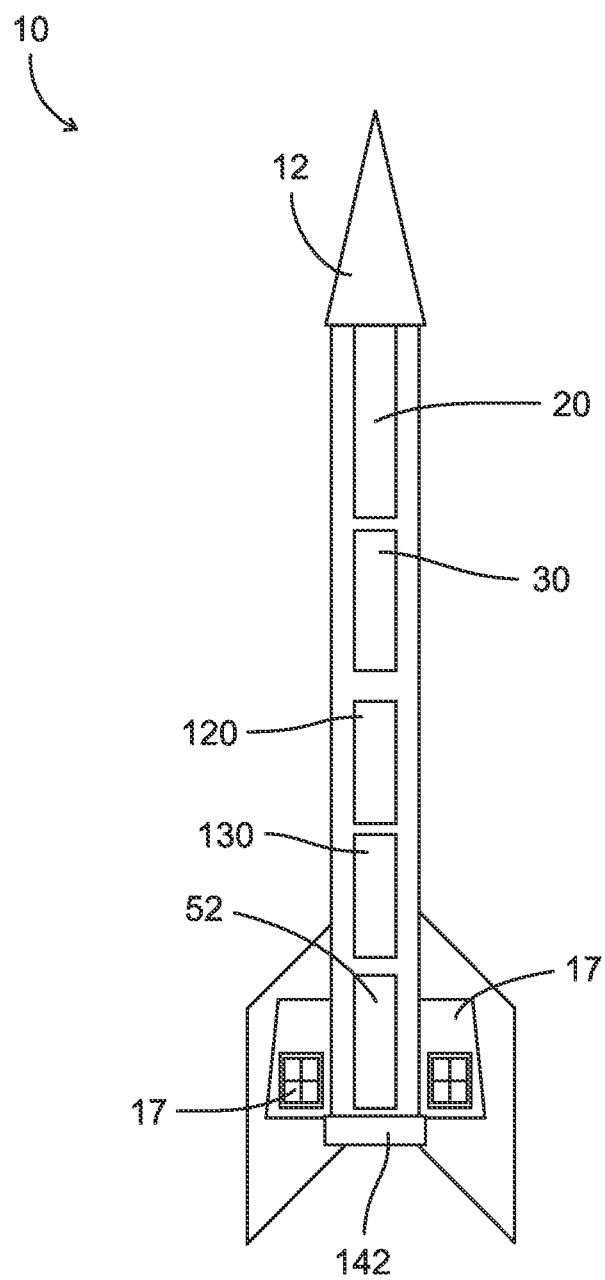
FIG. 12 is a schematic diagram of a preferred embodiment of the apparatus of the present invention.
Figure 13:
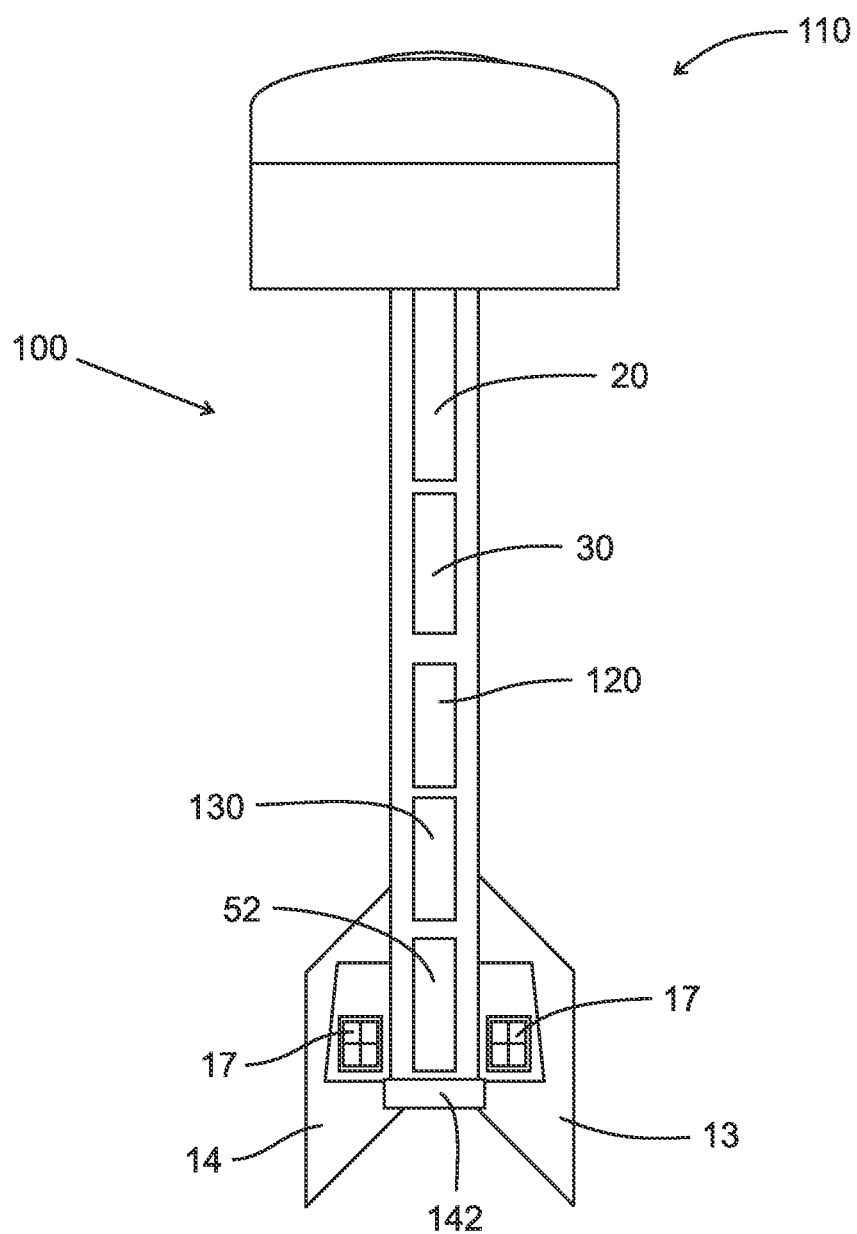
FIG. 13 is a schematic diagram of an alternative embodiment of the apparatus of the present invention.

FIG. 13 shows an alternative embodiment of sensor post or dart, designated generally by the numeral 100, with a modified head 110 that can stand when dart 100 cannot be mounted/imbedded/implanted in the earth (e.g., in rock formations). Head 110 can include a weighted (e.g., rubber, polymer, plastic) head or base that may wobble, but will not fall down in the wind. Dart or post 100 can include primary communications path 120, secondary or backup communications path 130, dominator 52, processor 30, and battery or batteries 20. Dart 100 can also include antenna 142 that can preferably be on the end distal from weighted head 110. For example, primary path 120 can be a satellite communications modem, and backup path 130 can be LTE. Communications device 100 can include one or more sensors 17, which can be CBRN/CSI sensors, for example. Sensor(s) 17 can be located on fins 13, 14 of device 100. As shown in FIG. 12, sensor dart 10 can also include a weight in nose 12, a primary communications path 120, a secondary or backup communications path 130, a dominator 52, processor 30, battery or batteries 20, and antenna 142, preferably located at the end distal of nose 12 of dart 10. Primary path 120 can be a satellite communications modem, and backup path 130 can be LTE, for example. Dart 10 can include sensor(s) 17, such as CBRN/CSI sensor(s), for example. In a preferred embodiment of the present invention, darts 10, 100 can have a distance of about 1,000 feet between each dart 10, 15, 100 that is part of the sensor fence system 23. The distance between darts 10, 15, 100 can vary though, and can be much closer together than 1,000 feet and/or much further apart than 1,000 feet.

Figure 14:
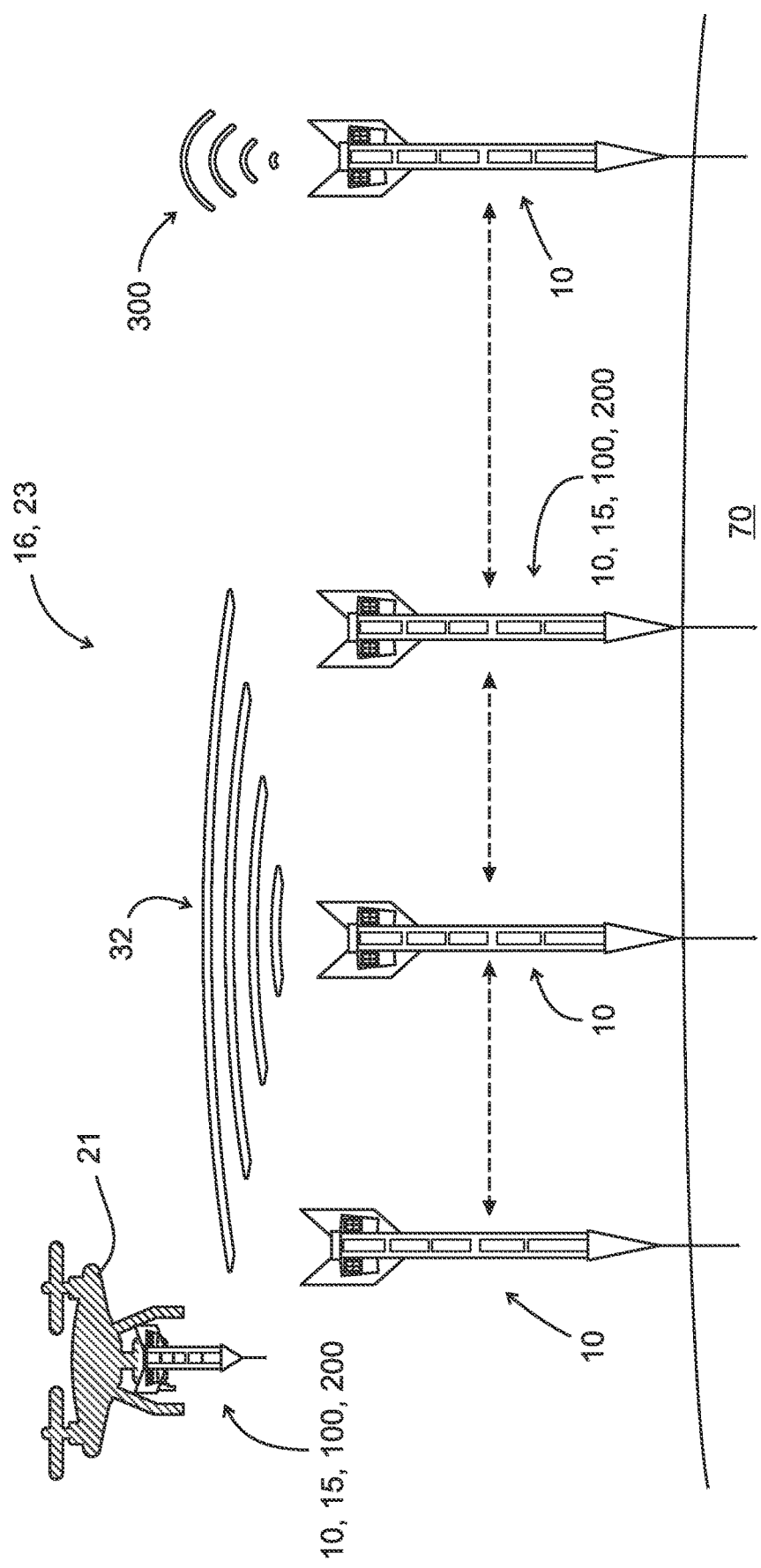
FIG. 14 is an illustration of a preferred embodiment of the apparatus and the system of the present invention, showing the deployment and partial embedding of various sensor posts or darts in the ground or earth's surface and the communications system between the various posts/components.
Figure 18:
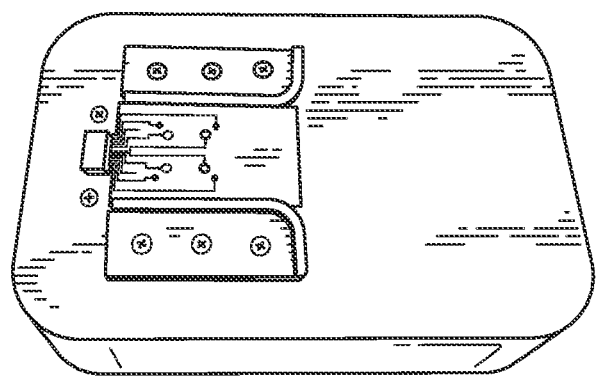
FIGS. 18-21 show various preferred embodiments of a wearable or handheld communications device apparatus of the present invention.
Figure 19:
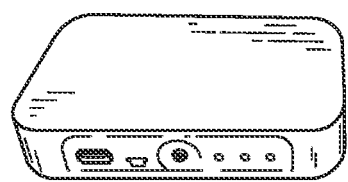
Figure 20:
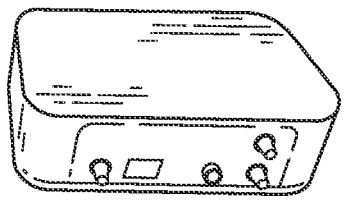
Figure 21:
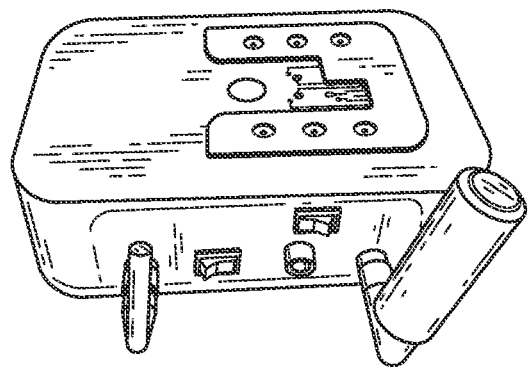

FIG. 14 is a preferred embodiment of the system of the present invention, showing how a sensor fence 16, 23 can be deployed and the method of use of the system. Each device 10, 100, 200 in the fence 23 can send and receive messages to each other, as well, as communicate in a chain to a gateway, post or dart 15 that can have wide area, satellite communications capabilities that can operate over a network such as the Outerlink network. These devices can be capable of being left behind in the field or air dropped by drone 21 or other aircraft. When an event occurs, the information can be uplinked, designated by the numeral 300, via satellite, for example. Mesh communication 32 can occur between darts 10, 15, 110, 200, as shown in FIG. 14.

FIGS. 15-17 show an alternative preferred embodiment of the apparatus of the present invention, designated generally by the numeral 200. Dart or post 200 can have nose or head 212, body, housing, or tube 211 and area 250, located distally from the location of head 212. Area 250 preferably includes handle 252 and end 256. Batteries are preferably located within tube 211. The electronic components or electronics of post 200 are preferably located within end 256. Electronic components of device 200 can include those mentioned in devices 10, 15, and/or 100. FIG. 17 shows an alternative embodiment of head 212 that can include arms 214 that are preferably connected to head 212 with hinges 213. Arms 214 can be retractable. Tip 215 of nose 212 can have cap 216. If arms 214 are not in use, their ends can be stored in cap 216. Cap 216 can be removed from tip 215 of head 212, which exposes arms 214 and allows them to rest on the ground 70, such as in a tripod configuration. This tripod configuration allows for dart or post 200 to be left in place where it is not possible to embed dart or post 200 in the ground or earth 70. Removing cap 216 exposes retractable arms 214 to place dart or post 200 on the ground 70.

List of Acronyms and Abbreviations

BIP Blow In Place
CBRN Chemical/Biological/Radiation/Nuclear
CARDS Clear Alert Rapid Detection System
CSI Clear Scientific Inc.
Comms Communications
GPS Global positioning system
ID Identification
IoT Internet of Things
LoRa Long Range
LTE Long Term Evolution RF Radio Frequency
RFID Radio Frequency Identification
Sat Satellite
SatCom Satellite communications
WiFi Wireless Fidelity

PARTS LIST

The following is a list of parts and materials suitable for use in the present invention:
Parts Number Description
10 communication device/sensor post/sensor dart
11 fuselage/housing/tube/body/container
12 nose/cone/head
13 fin
14 fin
15 gateway dart/gateway variant device
16 single tethered sensor fence/fence system
17 sensor
18 solar panel/solar tape
19 battery
20 battery
21 drone
22 antenna
23 sensor fence/tethered fence system
25 battery charging circuit
28 antenna
30 processor
32 mesh network communication protocol/long range (LoRa) of processor 30
35 accelerometer
40 analog to digital converter
42 antenna
45 printed circuit board
50 area
52 sensor trigger/dominator
55 chemical/bio sensor
60 modem
65 leave behind device/circuitry
68 gyroscope
70 battlefield/ground/earth's surface
80 environmental sensor (such as a wind long range sensor—also known as a Wind Lora)
90 central gateway
100 sensor dart/post/communication device
110 head of dart/post 100
120 primary communications path of dart 100
130 secondary/backup communications path of dart 100
142 antenna
200 communication device/sensor post/sensor dart
211 housing/tube
212 nose/head
213 hinge
214 arm
215 tip of nose 212
216 cap
250 area
252 handle
256 end
300 uplink of event All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A sensor fence apparatus, comprising
a) a plurality of spaced apart dart or rocket shaped posts or darts in contact with the earth's surface or an underlying terrain;
b) each dart or post having a housing, shell, or fuselage having an interior and an exterior, a plurality fins attached to the exterior of one of said housing, shell, or fuselage;
c) at least one sensor located on each fin of each said dart or post;
d) at least one processor located within the interior of the fuselage;
e) each post or dart having a power source;
f) each post having an output device;
g) wherein each of the at least one sensor of each said dart or post senses one or more of the following environmental parameters: humidity, temperature, wind, and particulates in the air that are hazardous or deadly;
h) wherein said output device transmits said one or more environmental parameters to one or more others of said posts or darts; and
i) wherein the plurality of spaced apart darts create a sensor fence.

2. The apparatus of claim 1, wherein said output device transmits the one or more environmental parameters over a wireless data communication network.

3. The apparatus of claim 1, wherein said output device transmits said one or more environmental parameters via satellite communications.

4. The apparatus of claim 1, wherein said output device transmits said one or more environmental parameters to one or more others of said posts or darts via a mesh network.

5. The apparatus of claim 1, further comprising wireless local area networking capabilities that allow for each post or dart to communicate with a tablet or smartphone or to connect to a wireless data communication network or satellite network.

6. The apparatus of claim 4, further comprising wireless local area networking capabilities that allow for each post or dart to communicate with a tablet or smartphone or to connect to a wireless data communication network or satellite network.

7. The apparatus of claim 1, further comprising a weighted tip at one end of each housing, shell, or fuselage.

8. The apparatus of claim 7, wherein said weighted tip includes a rubber, plastic, or polymeric material.

9. The apparatus of claim 1, further comprising a CBRN sensor.

10. A method of collecting and monitoring environmental data using the apparatus of claim 1 comprising the steps of:
a) equipping at least one of the spaced apart darts or rocket shaped posts or darts with the ability to transmit data over a wireless data communication network or satellite communications;
b) spacing the darts a maximum of 1640 feet apart to create a sensor fence;
c) sensing, via the at least one sensor of each dart or post, environmental parameters;
d) transmitting the environmental parameters sensed via step (c) to the at least one said dart or rocket shaped post or dart equipped with the ability to transmit data over a wireless data communication network or satellite communications of step (a); and
e) transmitting the data from said at least one dart or rocket shaped post or dart.

11. A sensor fence system, comprising:
a) a plurality of spaced apart communications devices including sensor posts or darts and at least one gateway post or dart;
b) each said sensor dart or post having the ability to communicate with one or more other of said sensor posts or darts;
c) wherein said communications devices each collect and transmit environmental data that includes one or more of the following parameters: humidity, temperature, wind, and particulates in the air that are hazardous or deadly;
d) wherein said communications devices are connected to a wireless data communication network;
e) wherein said at least one gateway post or dart comprises a satellite modem, antenna, and the ability to blow in place; and
f) wherein the plurality of spaced apart sensor darts or posts and at least one gateway post or dart create a sensor fence.

12. A method of collecting and monitoring environmental data using the system of claim 11 comprising the steps of:
a) air dropping the plurality of spaced apart communication devices from a drone or rotorcraft to the earth's surface;
b) utilizing the plurality of spaced apart communication devices to collect environmental data;
c) transmitting the environmental data to one or more of the other said communication devices; and
d) monitoring the environmental data collected in step "b" by the one or more communication devices.

13. A sensor and transmitter communications device, comprising:
a) a shell or container having an interior and an exterior, said container including one or more fins attached to the exterior of said container;
b) at least one sensor attached to a fin;
c) at least one processor located within the interior of the shell;
d) a power source;
e) a head comprising a weighted circular tip designed to not embed in the earth;
f) said shell or container having an output device; and
g) wherein in use, said shell or container is in contact with ground or soil, wherein said at least one sensor senses environmental data, and said output device transmits said environmental data to another said sensor and shell or container which is in contact with ground or soil.

14. The communications device of claim 13, wherein said output device transmits said environmental data over a wireless data communication network.

15. The communications device of claim 13, wherein said output device transmits said environmental data via satellite communications.

16. The communications device of claim 13, wherein said at least one sensor is a CBRN sensor.

17. The communications device of claim 13, wherein said weighted circular tip includes a rubber, plastic, or polymeric material.

18. The communications device of claim 13, further comprising a chemical sensor.

19. A method of collecting and monitoring environmental data using the device of claim 13 comprising the steps of:
a) air dropping the sensor and transmitter device from a drone or rotorcraft so that the device is in contact with ground or soil;
b) sensing environmental data from the at least one sensor of the device; and
c) transmitting the environmental data to another sensor and transmitter communications device which is in contact with ground or soil.

20. The method of claim 19, further comprising the step of providing wireless local area networking capabilities that allow for communication with a tablet or smartphone or to connect to a wider area network.

21. A sensor fence apparatus, comprising:
a) a plurality of spaced apart sensor posts or sensor darts, each sensor or dart comprising a head which includes a plurality of retractable arms which can rest on the ground when extended and which are designed to allow the posts or darts to rest on the ground when it is not possible to embed the darts or posts in the ground;
b) each said sensor post or sensor dart enabled to communicate with one or more other said sensor posts or sensor darts in a daisy chain fashion that connects each sensor post or sensor dart to another sensor post or sensor dart in an elongated series;
c) each said sensor post or sensor dart configured to collect and transmit environmental data that includes one or more of the following parameters: humidity, temperature, wind, particulates in the air that are hazardous or deadly;
d) wherein said sensor posts or sensor darts are each connected to a wireless data communication network;
e) wherein each said sensor post or sensor dart is configured to be air dropped;
f) wherein said sensor posts or sensor darts are each spaced from other said sensor posts or sensor darts by a distance of between about 900 and 1600 feet; and
g) wherein at least some of said sensor posts or sensor darts are configured to at least partially embed in the earth's surface when air dropped.

* * * * *